United States Patent [19]

Stark et al.

[11] Patent Number: 4,475,370
[45] Date of Patent: Oct. 9, 1984

[54] DEVICE FOR TREATING DENTAL CASTINGS

[75] Inventors: Marvin M. Stark, Los Altos Hills; Kenneth B. Soelberg, Menlo Park; Roger B. Pelzner, San Mateo; Mark S. Bogdan, Menlo Park, all of Calif.

[73] Assignee: Marvin M. Stark Research Foundation, Santa Clara, Calif.

[21] Appl. No.: 495,144

[22] Filed: May 16, 1983

[51] Int. Cl.³ .............................................. B21J 51/28
[52] U.S. Cl. ........................................... 72/53; 51/426
[58] Field of Search ...................... 72/53; 51/426, 424, 51/410; 241/40

[56] References Cited

U.S. PATENT DOCUMENTS

| 914,783 | 3/1909 | Boland | 51/426 |
| 2,441,441 | 5/1948 | Paasche | 51/426 |
| 3,019,522 | 2/1962 | Bluth et al. | 72/53 |
| 4,354,641 | 10/1982 | Smith | 241/40 |
| 4,432,169 | 2/1984 | Schultz et al. | 51/424 |

FOREIGN PATENT DOCUMENTS 501037  6/1930  Fed. Rep. of Germany ........ 241/40

Primary Examiner—Francis S. Husar
Assistant Examiner—Linda McLaughlin
Attorney, Agent, or Firm—Lothrop & West

[57] ABSTRACT

An apparatus for treating the surface of a dental inlay for a tooth has a cup enclosure with a restricted opening therein. A hollow stem is slidably received in the cup and releasably held in a chosen position. An inlay holder is at the end of the stem within the cup enclosure and in the path of a stream of grit particles projected from the reservoir through a nozzle extending through the opening into proximity with the inlay holder.

5 Claims, 3 Drawing Figures

U.S. Patent    Oct. 9, 1984    4,475,370
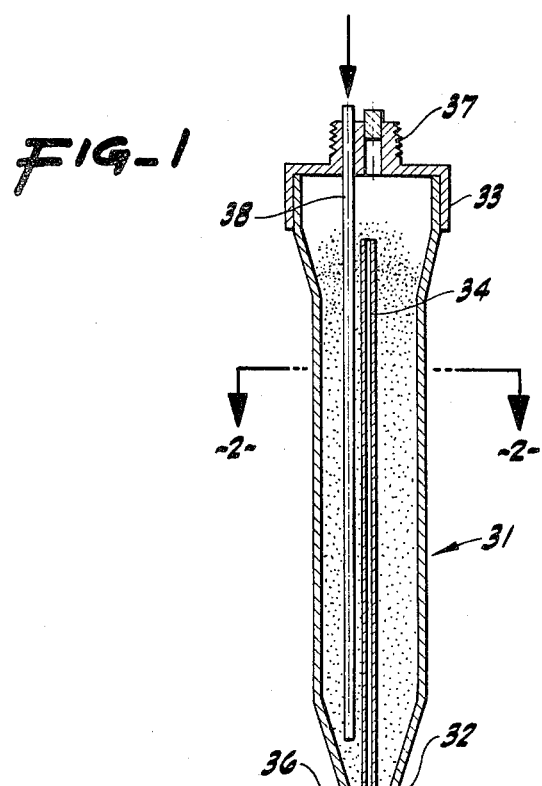
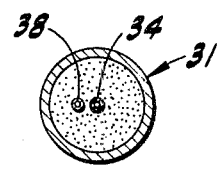
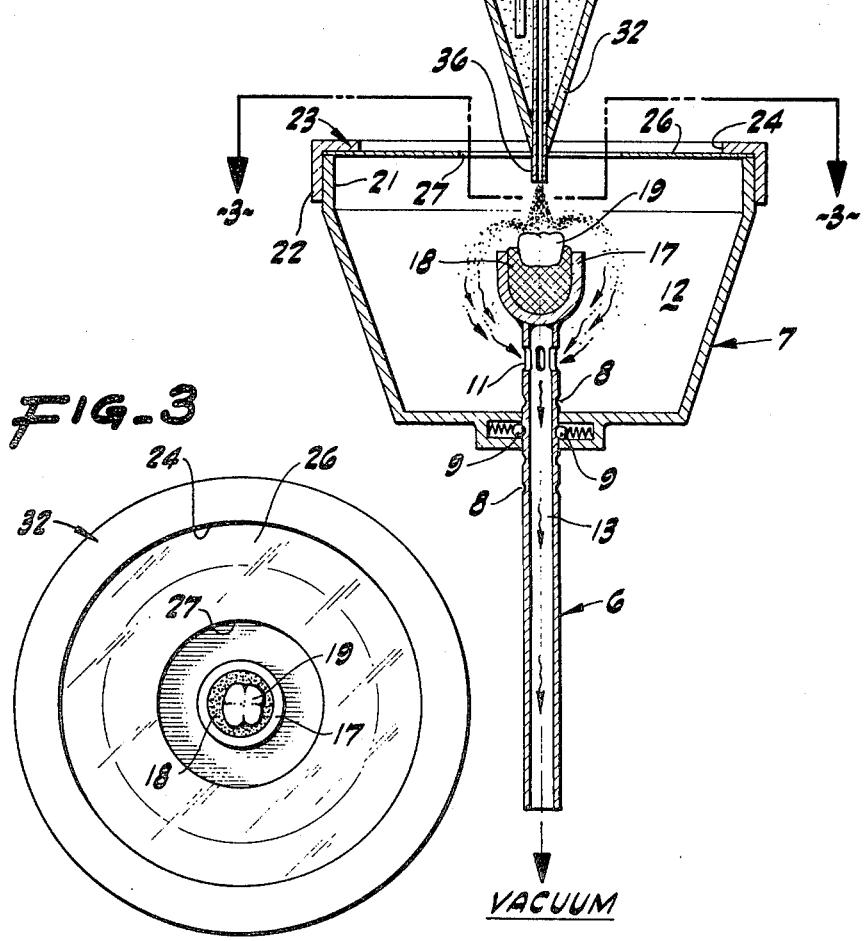
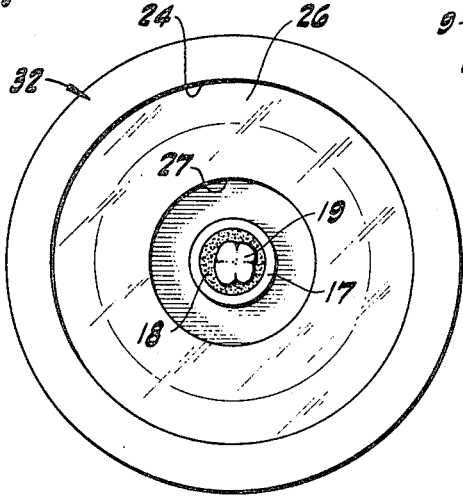

DEVICE FOR TREATING DENTAL CASTINGS

BRIEF SUMMARY OF THE INVENTION

For preparing the surface of a dental inlay for a tooth, there is a provided a temporary inlay holder including a hollow stem disposed within a cup enclosure having an aperture near the inlay holder through which a grit blasting gun can project in order forcibly to discharge grit carried by the gun against the exposed surface of an inlay in the holder. Preferably, the stem and the cup are relatively adjustable.

PRIOR ART

None is known to the applicants.

BRIEF DESCRIPTION OF THE DRAWINGS

FIG. 1 is a cross-section on a longitudinal plane through the apparatus of the invention.

FIG. 2 is a cross-section, the plane of which is indicated by the line 2—2 of FIG. 1.

FIG. 3 is a cross-section, the planes of which are indicated by the line 3—3 of FIG. 1.

DETAILED DESCRIPTION

There are many instances in the practice of dentistry in which it is helpful to provide a metal insert or inlay for a tooth. The inlay is usually a rough casting of a precious metal such as gold or silver and is cemented into a prepared portion of the tooth being repaired. The inlay casting as received from the mold sometimes has a generally unsatisfactory surface for cementing into the receptive cavity. We have therefore provided a means for improving the surface of the inlay so that it is adapted better for appropriate fixing into position.

For that purpose, we provide a hollow stem 6 having a generally sliding engagement with a larger surrounding cup 7. The interengagement of the stem and cup is preferably such that they may be positioned in different axial relationships to each other. For that purpose, the stem 6 has one or more holes 8 or grooves in its periphery. These are receptive of spring-pressed retaining balls 9 or the like. The stem at its remote end is adapted to be connected to a tube or other suitable flexible connector to a source of vacuum such as that normally found in any dental office.

The stem 6 at its upper end is provided with a number of openings 11 through its walls to afford ready access between the interior 12 of the cup and the interior 13 of the stem. At its upper end the stem is permanently secured to a receiving device 17 or work holder shaped like a thimble and in which is lodged a body 18 of a putty-like material. An inlay 19 or the like can easily be embedded temporarily in the putty-like material and thus held generally in any one or more selected positions in the work holder for subsequent work on the inlay.

The cup 7 is of a generally tapered configuration and ends at one margin in a generally circular cylindrical rim 21 adapted to receive a comparable rim 22 on a cover 23. The cover has a relatively large opening 24. A portion of the cup is masked or shielded by a transparent plastic sheet 26 having a port 27 therein big enough to pass the receiving device or work holder 17 therethrough when the hollow stem is lifted. Access to the interior 12 of the cup can be readily attained by removing the cover. Even with the cover in place, the operations within the cup can be easily seen through the transparent cover 26 at any time.

Cooperating with the structure just described, there is a reservoir 31 of generally tubular shape having a reduced lower end 32 and having a closure cap 33 thereon. The reservoir has a central tube 34 projecting therefrom to afford a nozzle 36. The lower ends of the receptacle and of the nozzle are readily received through the port 27 in the transparent cover 26. There is a connector 37 on the closure cap 33 carrying a pipe 38 extending alongside the tube 34 to a point near the lower end of the reservoir 31. Compressed air, readily available in a dental office, is furnished through a fitting (not shown) engaging the connector 37.

In use, the reservoir 31 is partly or entirely filled with an appropriate grit or abrasive such as small particles of a hard material. Aluminum oxide particles of about 2.5 microns in size are effective. The vacuum and compressed air connections are made. Compressed air entering through the pipe 38 stirs up and agitates the grit particles and causes them to be buoyant within the reservoir 31 so that some of them entrain in and flow outwardly through the center tube 34 and the nozzle 36 into the interior of the cup 7.

Preferably, the reservoir 31 is held and directed or aimed so that the particles of grit impinge directly upon various surface areas of the inlay 19 and rework the surface to afford a series of micropores. These are not normally visible to the naked eye but do show readily upon inspection by a scanning electro-microscope. The inlay 19 is positioned one or more times in the putty-like holding body 18 so that any and all parts of the inlay, both external and internal, can be treated. When the treatment has been completed to the user's satisfaction, the reservoir 31 is withdrawn from the port 27 in the sheet 26, the cover 23 is removed, and the inlay 19 is taken out of the holding matrix 18. The inlay can then be appropriately installed.

It has been found that with this surface conditioning treatment, surface impurities are removed and there is afforded a slightly pocked or matte or irregular surface. This assists the operator to detect occlusal proximal interferences. Furthermore, the anchoring of the inlay in the tooth cavity with the customary materials is substantially improved.

We claim:

1. A device for treating the surface of a dental casting comprising a hollow stem, a dental casting holder disposed on one end of said stem and adapted to contain putty-like material, a cup on said stem and substantially encompassing said dental casting holder, a cover on said cup having a central opening therein substantially in axial alignment with and of a size to pass said dental casting holder axially therethrough, and means in said stem affording openings providing communication between the interior of said cup and the interior of said hollow stem for passing granular material from said cup through said openings into the interior of said stem.

2. A device as in claim 1 including deformable casting-receiving material in said dental casting holder.

3. A device as in claim 1 including a grit reservoir having a discharge nozzle receivable through said central opening in said cover and extending into said cup to the vicinity of said dental casting holder.

4. A device as in claim 1 in which said stem and said cup are relatively slidable, and means for holding said stem and said cup against relative sliding movement in at least one relative position thereof.

5. A device for treating the surface of a dental casting comprising a hollow stem extending along an axis, a dental casting holder open at one end and at the other end coaxially mounted on the end of said stem, said casting holder being of a thimble-like configuration adapted to receive a body of putty-like material into which said dental casting can be embedded with said surface exposed, a cup coaxially disposed on said stem and surrounding said casting holder, means in said cup for admitting granular material thereto, and means in said stem for passing said granular material from said cup into the interior of said stem.

* * * * *